US012478486B1

(12) United States Patent
Nelson et al.

(10) Patent No.: US 12,478,486 B1
(45) Date of Patent: Nov. 25, 2025

(54) FUNCTIONAL COSMETIC PROSTHETIC FINGER

(71) Applicant: FIXADIGIT, LLC, Clear Lake, IA (US)

(72) Inventors: Terry Lee Nelson, Clear Lake, IA (US); Dylan Lee Petersen, Clear Lake, IA (US); Angie Lee Moore, Clear Lake, IA (US); Staci Ann Andrea, Clear Lake, IA (US)

( * ) Notice: Subject to any disclaimer, the term of this patent is extended or adjusted under 35 U.S.C. 154(b) by 0 days.

(21) Appl. No.: 19/063,994

(22) Filed: Feb. 26, 2025

Related U.S. Application Data

(60) Provisional application No. 63/562,015, filed on Mar. 6, 2024.

(51) Int. Cl.
*A61F 2/58* (2006.01)
*A61F 2/50* (2006.01)

(52) U.S. Cl.
CPC ...... *A61F 2/586* (2013.01); *A61F 2002/5038* (2013.01)

(58) Field of Classification Search
CPC ........................... A61F 2/586; A61F 2002/587
See application file for complete search history.

(56) References Cited

U.S. PATENT DOCUMENTS 1,498,029 A * 6/1924 Giles ...................... A61F 2/586 623/57
2,867,819 A * 1/1959 George .................. A61F 2/586 623/63
7,361,197 B2 * 4/2008 Winfrey .................. A61F 2/583 623/64
9,629,731 B2 * 4/2017 Thompson, Jr. .......... A61F 2/78
11,382,772 B2 * 7/2022 Bravo Castillo ....... A61F 2/586
2022/0054283 A1 2/2022 Thompson, Jr.
2022/0296391 A1 * 9/2022 Popovic .................. A61F 2/586
2023/0056134 A1 * 2/2023 McClellan .............. A61F 2/586

FOREIGN PATENT DOCUMENTS

WO WO-2025111301 A1 * 5/2025 ............ A61F 2/586

OTHER PUBLICATIONS

Artificial Finger, JPH05161667, Morita (Year: 1993).*

* cited by examiner

*Primary Examiner* — Bruce E Snow
(74) *Attorney, Agent, or Firm* — Brian S. Steinberger; Hilary F. Steinberger; Steinberger IP Law

(57) ABSTRACT

Devices, systems, and methods for providing a functional cosmetic prosthetic finger, that can especially be used for a missing pinky finger down to the knuckle of the missing pinky finger. The prosthetic finger can include three stacked members that are each pivotally attached to one another. The top member can include a single side ring, and the lower member can include a pair of side-by-side rings. The prosthetic finger can expand and bend with the adjacent finger. The prosthetic finger can further be used for a missing fourth finger, missing middle finger, and missing index finger. The cosmetic device can be made from plastic, composites, metals, combinations thereof, different colors, and the like.

19 Claims, 13 Drawing Sheets

FUNCTIONAL COSMETIC PROSTHETIC FINGER

CROSS REFERENCE TO RELATED APPLICATIONS

This application claims the benefit of priority to U.S. Provisional Application Ser. No. 63/562,015 filed Mar. 6, 2024. The entire disclosure of each of the application listed in this paragraph are incorporated herein by specific reference thereto.

FIELD OF INVENTION

This invention relates to prosthetics, and in particular to devices, systems, and methods for providing a functional cosmetic prosthetic finger in place of a missing digit finger on a hand.

BACKGROUND AND PRIOR ART

There are some 50,000 injuries in the United States every year where a person loses at least part of a finger. When a person loses a finger, finger segment of a fingertip, the result is impaired performance of the hand to perform many basic tasks. For example, with a missing finger or fingertip, the task of typing on a computer keyboard or portable phone, or dialing on a telephone becomes significantly more difficult. These types of tasks generally require precise actions that need to be done by individual fingers.

In addition to allowing the performance of precise physical actions, individual fingers further provide an increased ability to grip and handle items. For example, when holding an item in the hand, the weight of the item is dispersed through all the fingers.

By varying the force used by each finger on the holder's hand, the holder is able to manipulate the item in a myriad of ways. However, if the holder is missing all or a part of a single digit, this freedom of manipulation and number of degrees through which the holder can manipulate the item is drastically decreased.

Many types of prosthetic fingers have been used primarily for cosmetic purposes and not as substitute for the missing finger. The cosmetic prosthetic fingers provide little or no functionality for the holder.

Attempts have been made to provide prosthetic fingers with some functionality. See for example, U.S. Published Patent Application 2022/0054283 to Thompson, Jr. et al., which is incorporated by reference. However, this Thompson '283 requires the use of a Y shaped rocker mechanism with a plurality of pivot points and a plurality that can be difficult and expensive to manufacture.

U.S. Published Patent Application 2023/0056134 to McClellan et al., which is incorporated by reference shows and describes a "finger prosthetic", title, that requires the prosthetic with a "base piece configured to fit on a proximal phalanx portion of the amputated finger", abstract. The McClellan '134 device requires that there must be at least a portion of the base of the missing finger to exist. As such, the McClellan '134 device does not appear to be able to work with someone missing their entire finger. For example, a victim having their entire pinky missing down to the knuckle would not be able to use the McClellan '134 device.

Thus, the need exists for solutions to the above problems with the prior art.

SUMMARY OF THE INVENTION

A primary objective of the present invention is to provide devices, systems, and methods for providing a functional prosthetic finger that it is fully customizable and modifiable by the user by using methods such as wearing above an existing ring, or the use of ring-sizers, thus allowing for the normal swelling of tissue and muscles after an amputation and in the healing phase due to daily overuse and temperature changes. (After amputation occurs, the neighboring fingers will never remain a consistent size due to trauma and healing.) The device will be available for both left and right-handed users, as well as the cosmetic replacement of any of the first through fourth digits. (Our test subject was replacing the fourth finger on the right hand, anchoring by the second and third fingers.).

A secondary objective of the present invention, which is to provide devices, systems, and methods for providing a functional prosthetic finger, is the aesthetically pleasing option to add or remove a cosmetic fingernail to the tip of the prosthetic, once again allowing the user to not only customize the appearance of the prosthetic, but also allowing the user the added benefit of treating the prosthetic as they would any of their other fingers, giving the added benefit of increased self esteem, allowing the prosthetic to feel like a normal part of their daily life, which is something that is missing from previous art.

A preferred embodiment of the functional cosmetic prosthetic finger for a missing pinky finger, can include a generally cylindrical base section having an upper end and a lower end, two side by side rings extending sideways from a left side of the base section, a tip section having a generally cylindrical configuration with an upwardly extending top and a bottom, one ring extending sideways from a left side of the tip section, the one ring being parallel to the two side by side rings of the base section, and a pivotal connection between the bottom of the tip section and the lower end of the base section, wherein the lower end of the base section is adapted positioned adjacent to what would be the knuckle of the missing finger, while the right one of the side by side rings, and the one ring are adapted to be slid over a third finger, and the right one of the side by side rings is adapted to be slid over a middle finger, so that prosthetic finger bends at the pivotal connection in unison with the third finger bending in position.

Further objects and advantages of this invention will be apparent from the following detailed description of the presently preferred embodiments which are illustrated schematically in the accompanying drawings.

BRIEF DESCRIPTION OF THE FIGURES

The drawing figures depict one or more implementations in accord with the present concepts, by way of example only, not by way of limitations. In the figures, like reference numerals refer to the same or similar elements.

DESCRIPTION OF THE PREFERRED EMBODIMENTS

Figure 1:
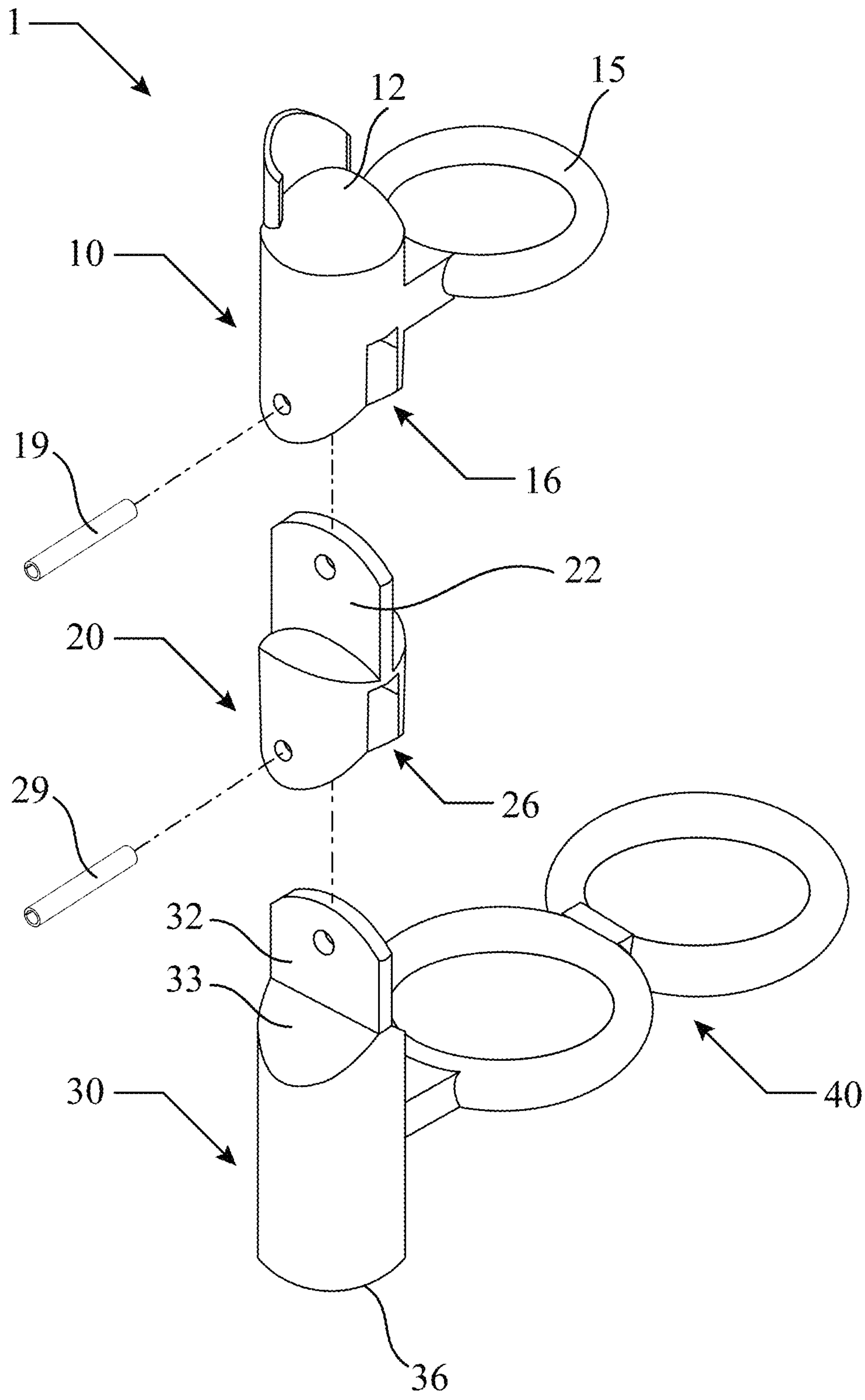
FIG. 1 is an exploded perspective view of the novel functional cosmetic prosthetic finger.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

In the Summary above and in the Detailed Description of Preferred Embodiments and in the accompanying drawings, reference is made to particular features (including method steps) of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments.

Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise specifically noted, articles depicted in the drawings are not necessarily drawn to scale.

A preferred embodiment of the invention is for use of the prosthetic finger being used when the entire pinky is missing down to the knuckle.

A list of component labels will now be described.

Figure 2:
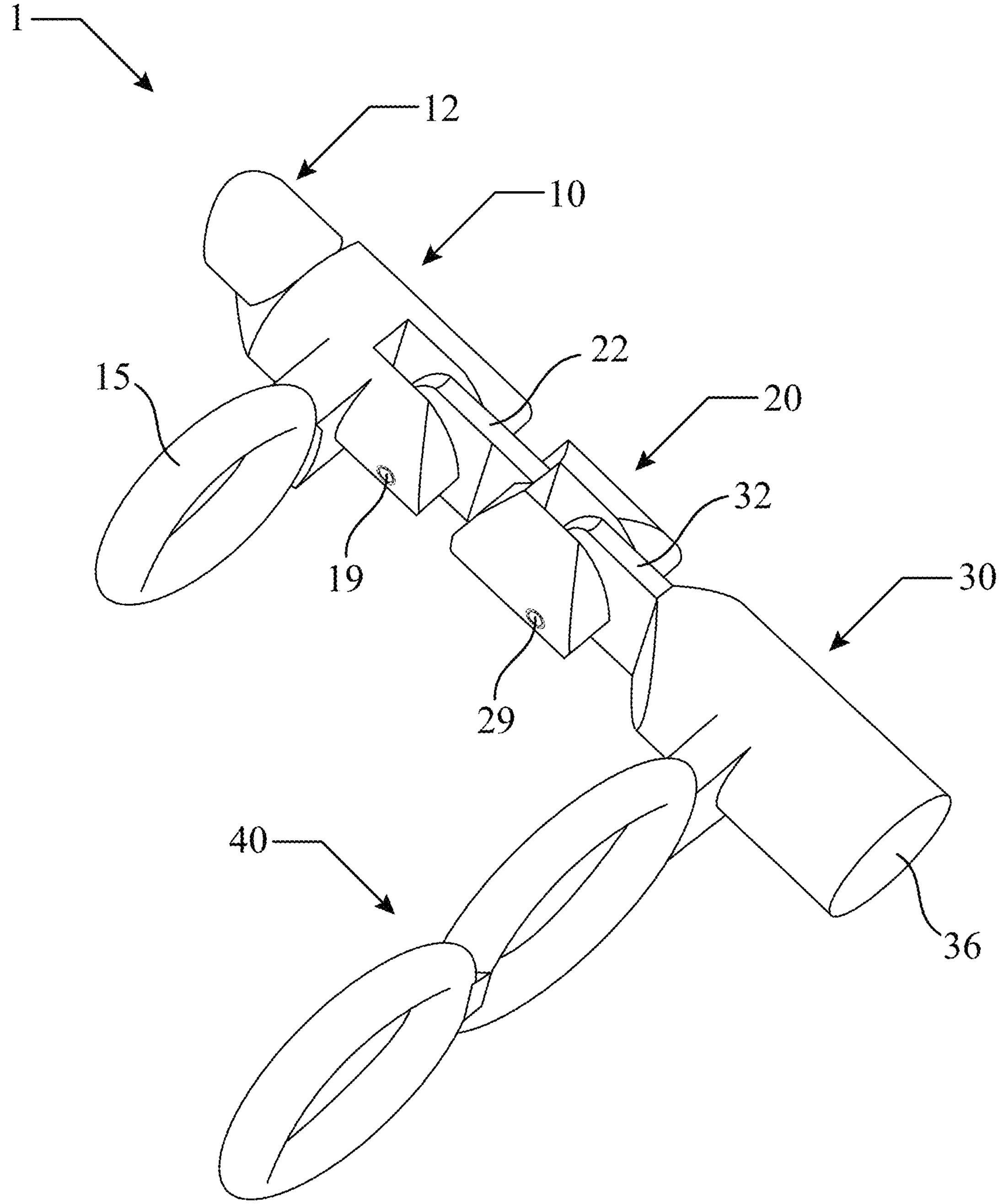
FIG. 2 is an assembled upper perspective view of the functional cosmetic prosthetic finger of FIG. 1.

1 prosthetic finger
10 top upper finger member
12 finger nail portion extending upward from dome top
15 side protruding ring
16 lower facing channel formed between pair of downwardly extending side walls
19 pivot pin
20 middle finger member
22 upper extending protruding tab
26 lower facing channel formed between pair of downwardly extending side walls
29 pivot pin
30 lower finger member
32 upper extending protruding tab
33 inwardly slanting sides
36 flat bottom end
40 pair of side-by-side rings extending to a side of lower finger member FIG. 1 is an exploded perspective view of the novel functional cosmetic prosthetic finger 1 that can include top finger member 10, pivotally attached to middle finger member 20, which is pivotally attached to lower finger member 30. FIG. 2 is an assembled upper perspective view of the functional cosmetic prosthetic finger of FIG. 1.

Members 10, 20 and 30 can be made from injection molded plastic, metal, composite material, combinations thereof and the like.

Top member 10 can have a generally cylindrical shape with a finger nail portion 12 extending upward from a dome top. A single side protruding ring 15 can extend to one side of a generally cylindrical portion of the top member 10. A lower facing channel 16 formed between a pair of downwardly extending side walls can be located on the bottom of the top member.

Middle finger member 20 can have a generally cylindrical shape with an upper extending protruding tab 22 extending upward.

The upper extending protruding tab 22 can be inserted in the lower facing channel 16 of the top upper finger member 10. A pivoting pin 19 can be inserted through side through-holes in the downwardly extending side walls 16 of the top finger member 10 through a through-hole in the upper extending protruding tab 22, which allows top upper finger member 10 to pivot relative to the middle finger member 20.

Lower finger member 30 can have a generally cylindrical shape with an upper extending protruding tab 32 extending upward inwardly slanting sides 33 of the top of the lower finger member 30.

A pair of side-by-side rings 40 extending sideways from a midportion of the lower finger member 30. The side-by-side rings 40 are located parallel to and spaced apart under the side protruding ring 15. The left one of the side-by-side rings 40 being located parallel to the side protruding ring 15, and each having a central axis in the same plane.

The upper extending protruding tab 32 can be inserted in the lower facing channel 26 of the top middle finger member 20. A pivoting pin 29 can be inserted through side through-holes in the downwardly extending side walls 26 of the middle finger member 20 through a through-hole in the upper extending protruding tab 32, which allows top middle finger member 20 to pivot relative to the lower finger member 30.

The bottom of the lower finger member 30 can be generally flat in order to be adjacent to the knuckle portion of the finger that the prosthetic finger 1 is being used to replace.

Figure 3:
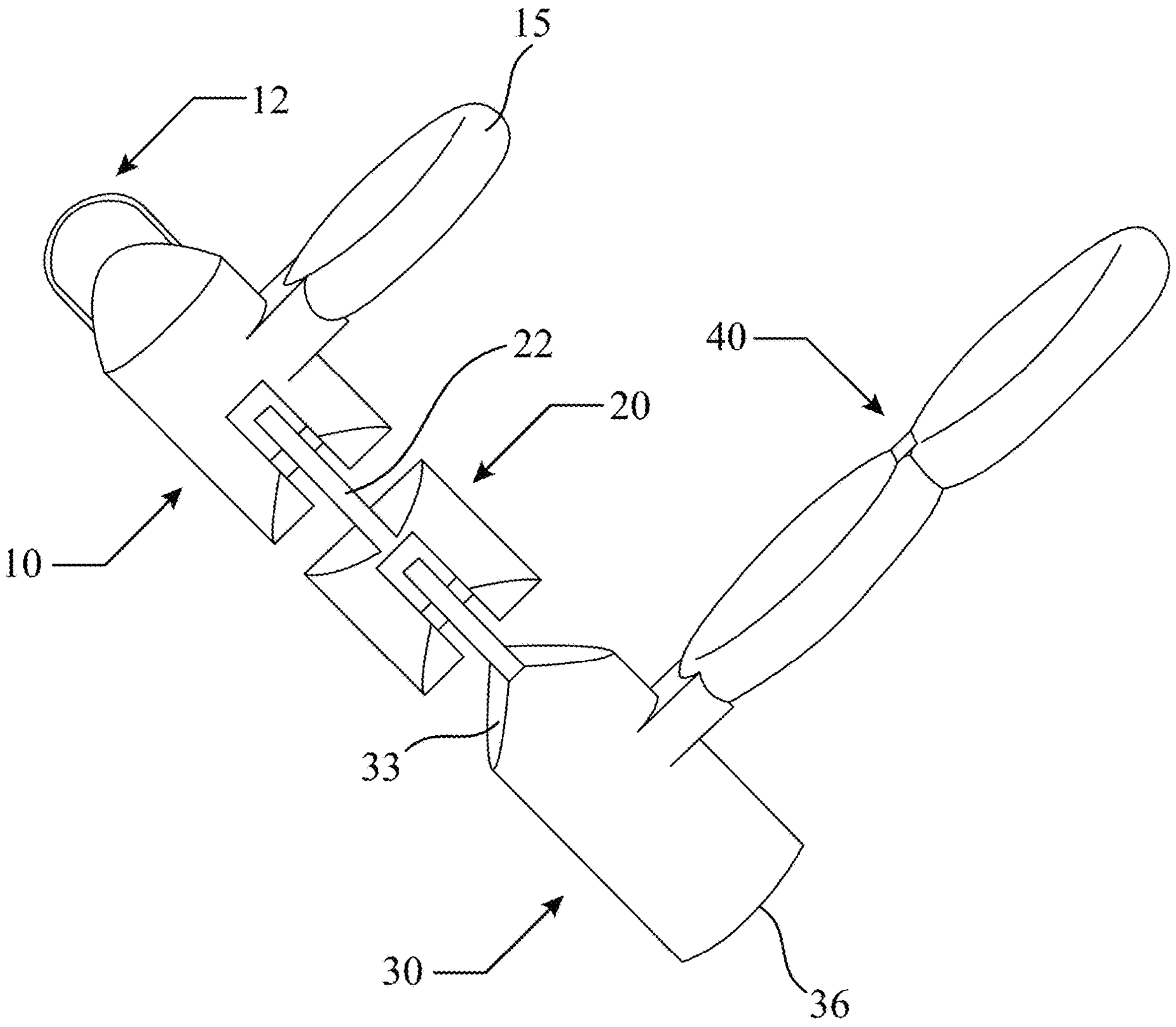
FIG. 3 is an assembled lower perspective view of the functions prosthetic finger of FIG. 1.

FIG. 3 is an assembled lower perspective view of the functional prosthetic finger 1 of FIG. 1.

Figure 4:
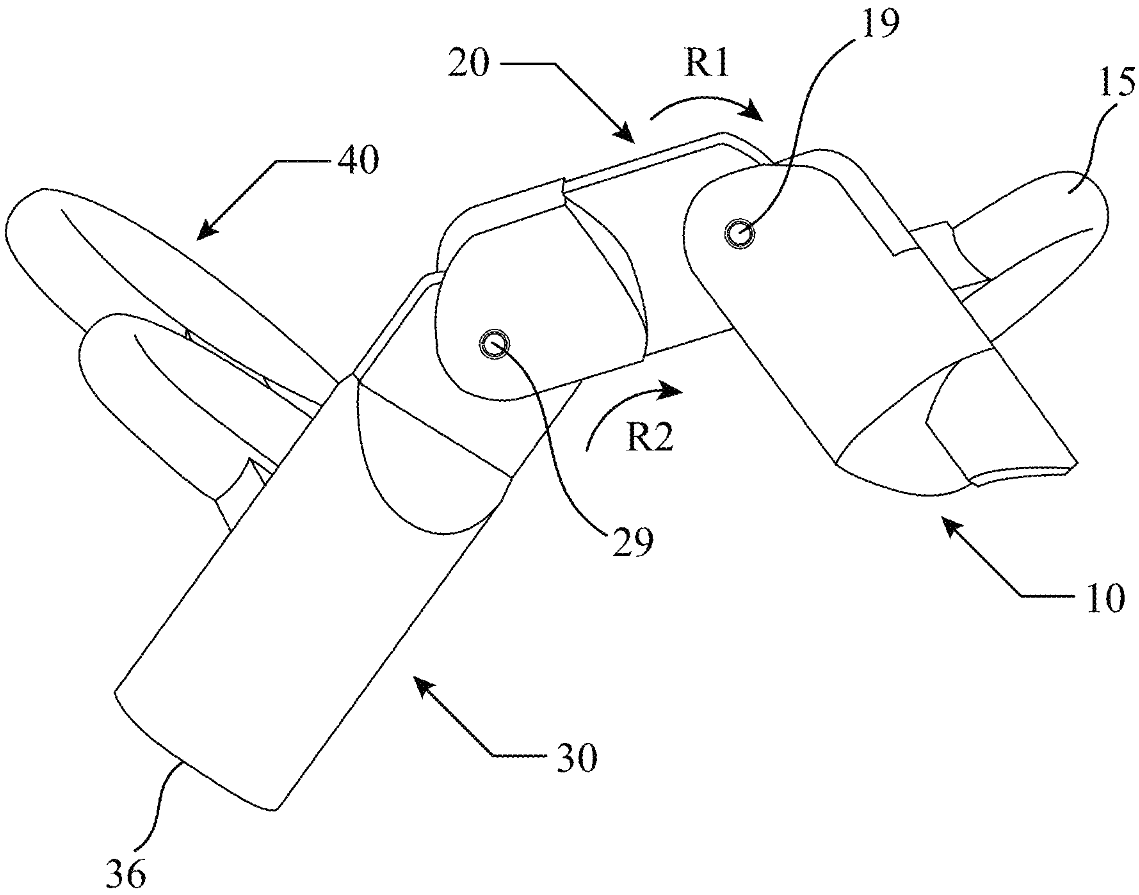
FIG. 4 is a perspective view of the assembled prosthetic finger of FIGS. 1-3 in one unique position.

FIG. 4 is a perspective view of the assembled prosthetic finger 1 of FIGS. 1-3 in one unique position. The upper finger member 10 can be rotated in the direction R1 relative to middle finger member 20, which can be rotated in the direction R2 relative to lower member 30.

Figure 5:
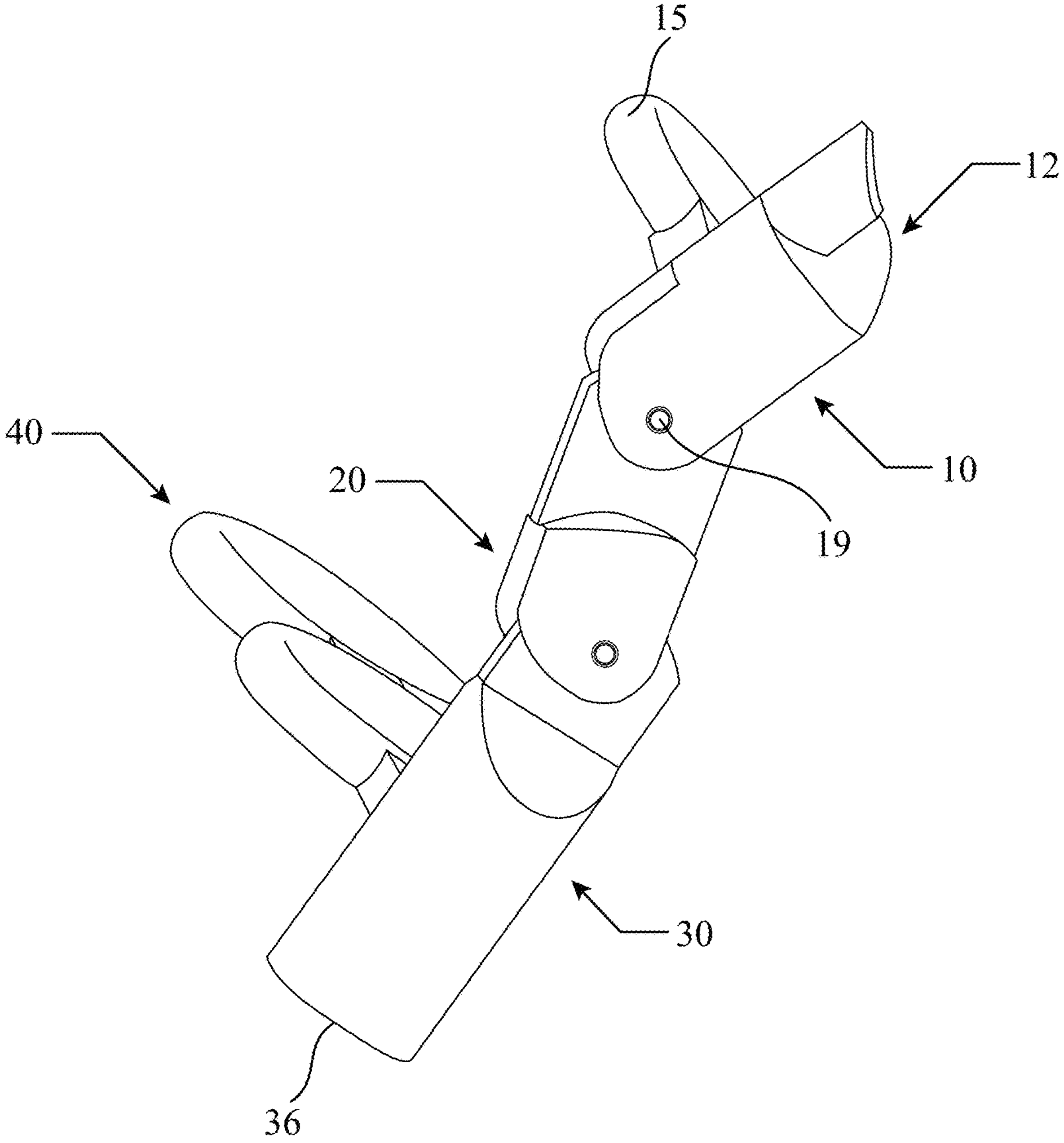
FIG. 5 is a perspective view of the assembled prosthetic finger of FIGS. 1-3 in a second unique position.

FIG. 5 is a perspective view of the assembled prosthetic finger of FIGS. 1-3 in a second unique position with upper member 10 rotated relative to middle member 20, which can be rotated relative to lower member 30.

Figure 6:
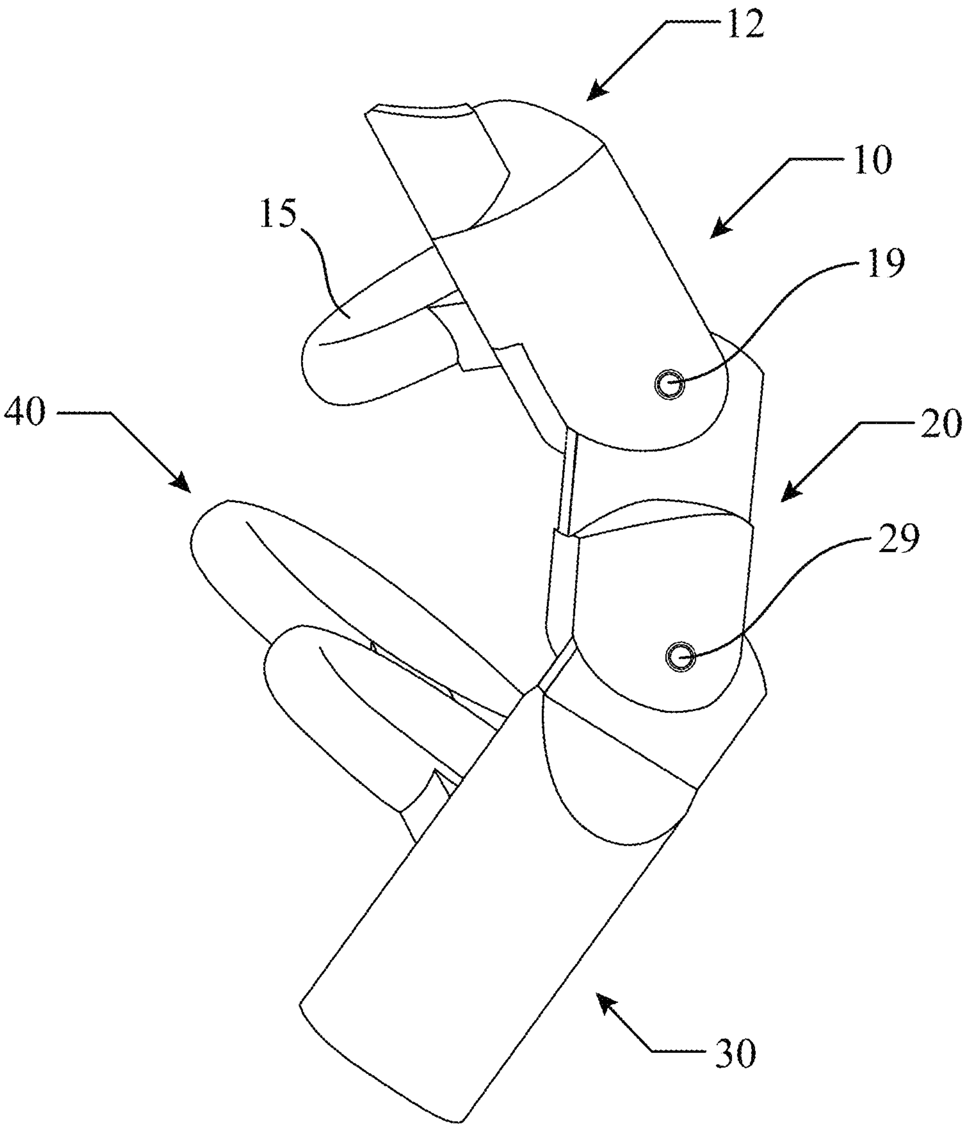
FIG. 6 is a perspective view of the assembled prosthetic finger of FIGS. 1-3 in a third unique position.

FIG. 6 is a perspective view of the assembled prosthetic finger 1 of FIGS. 1-3 in a third unique position with upper member 20 rotated in a different direction relative to middle member 20, which can be further rotated relative to lower member 30.

Figure 7:
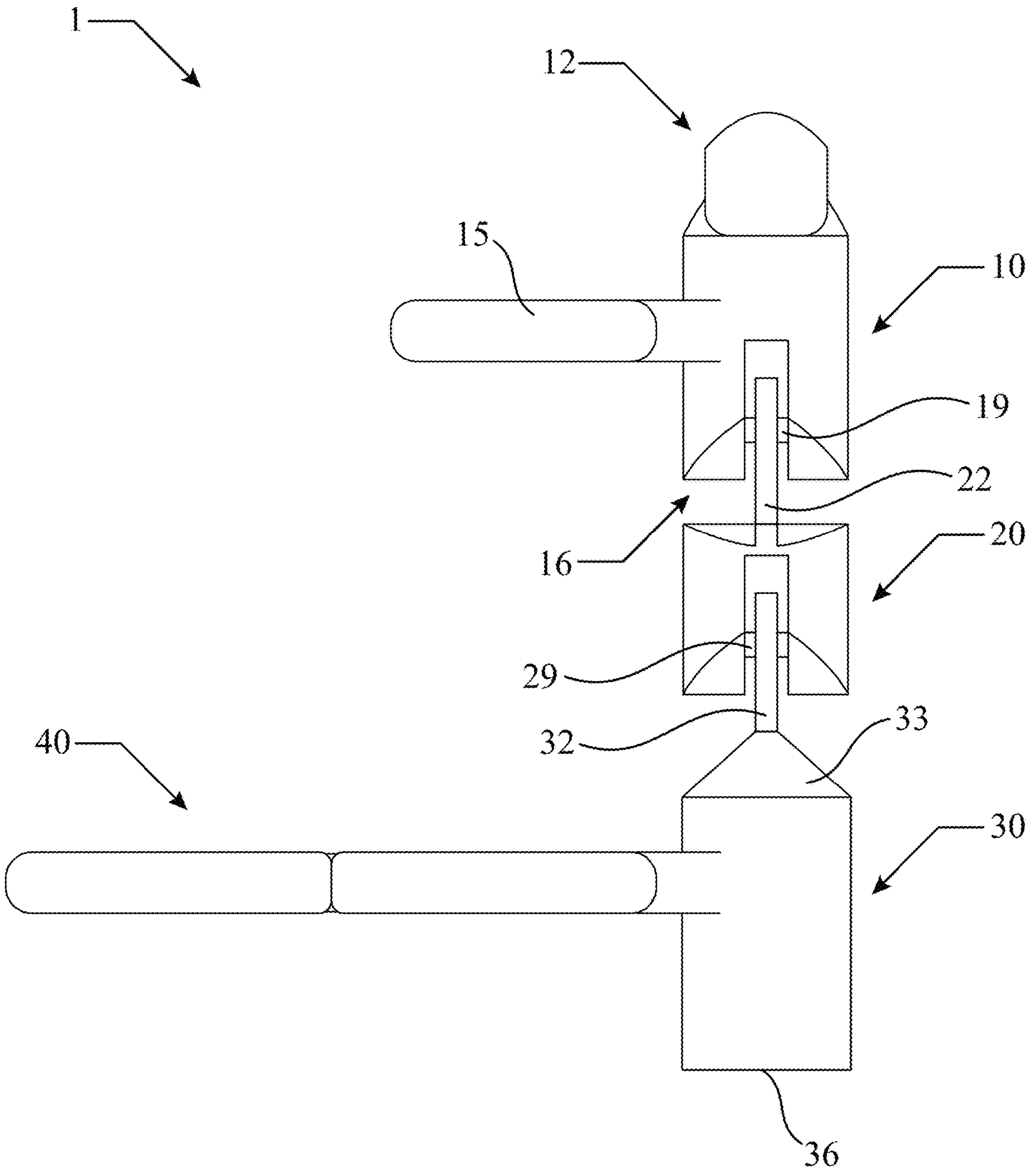
FIG. 7 is a front view of the assembled upper perspective view of the functional cosmetic prosthetic finger of FIG. 2.

FIG. 7 is a front view of the assembled upper perspective view of the functional cosmetic prosthetic finger 1 of FIG. 2.

Figure 8:
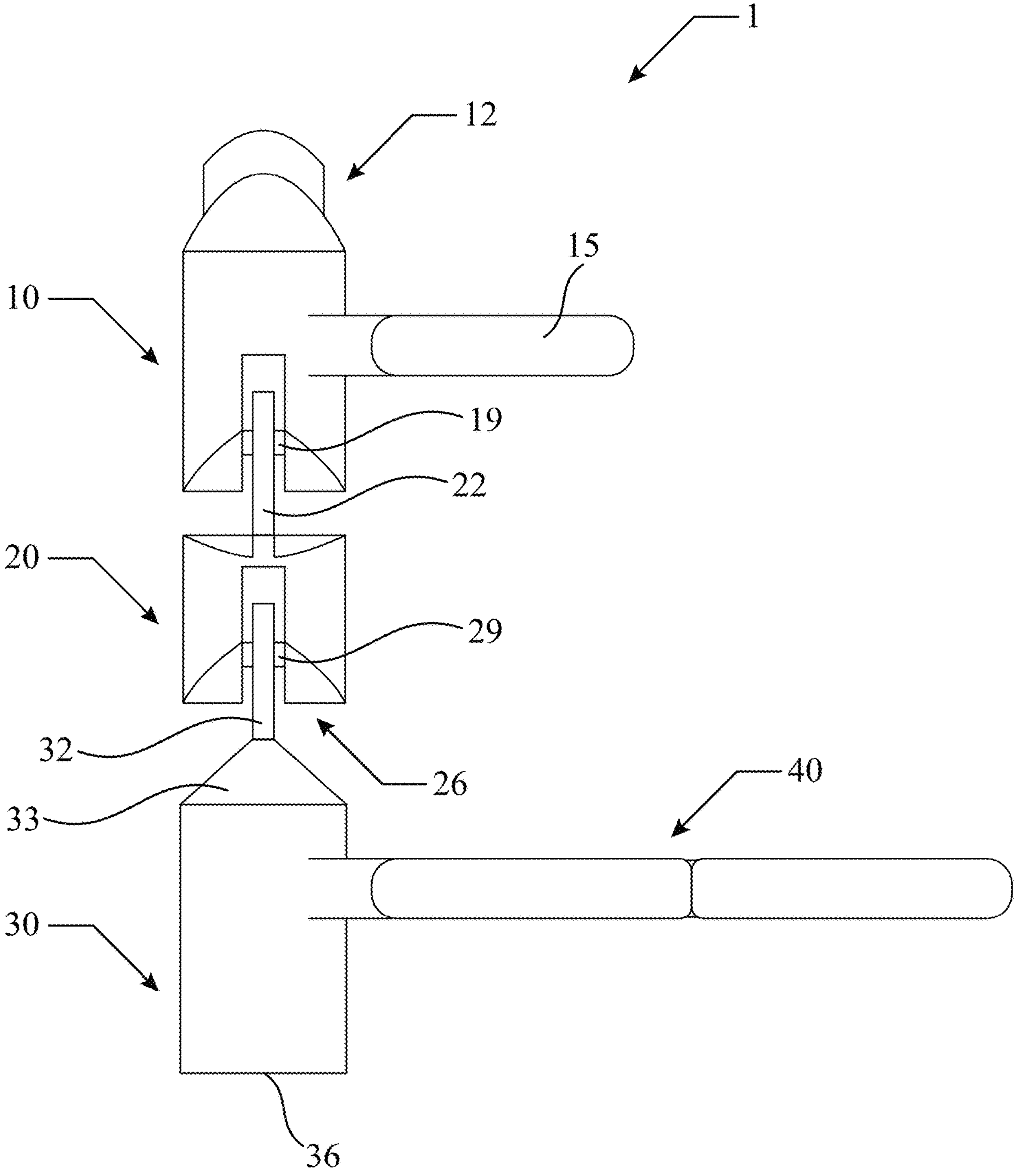
FIG. 8 is a back view of the assembled upper perspective view of the functional cosmetic prosthetic finger of FIG. 2.

FIG. 8 is a back view of the assembled upper perspective view of the functional cosmetic prosthetic finger 1 of FIG. 2.

Figure 9:
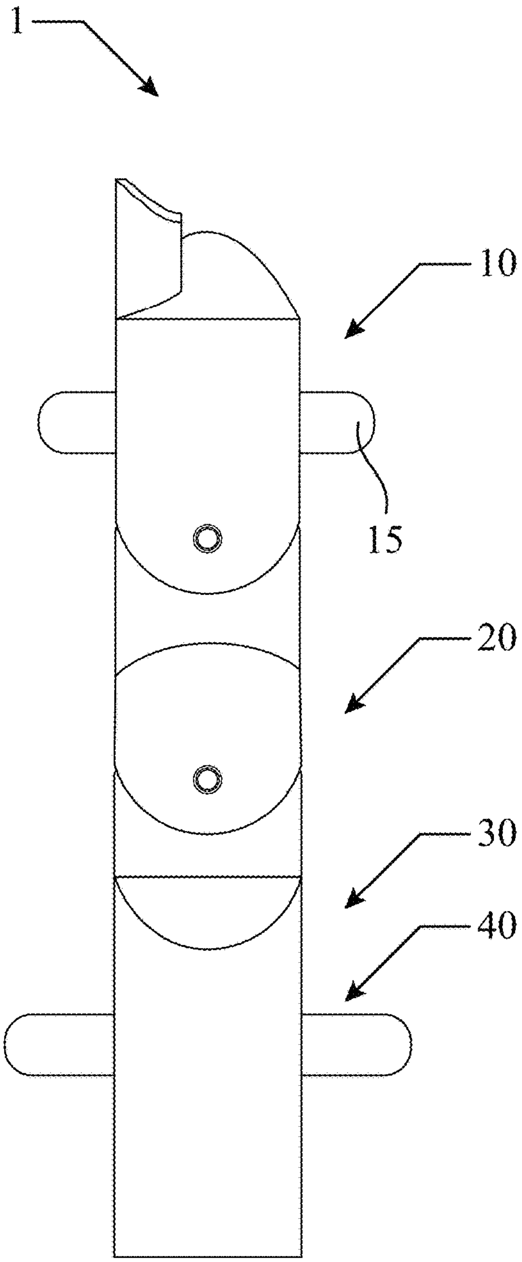
FIG. 9 is a left side view of the assembled upper perspective view of the functional cosmetic prosthetic finger of FIG. 2.

FIG. 9 is a left side view of the assembled upper perspective view of the functional cosmetic prosthetic finger 1 of FIG. 2.

Figure 10:
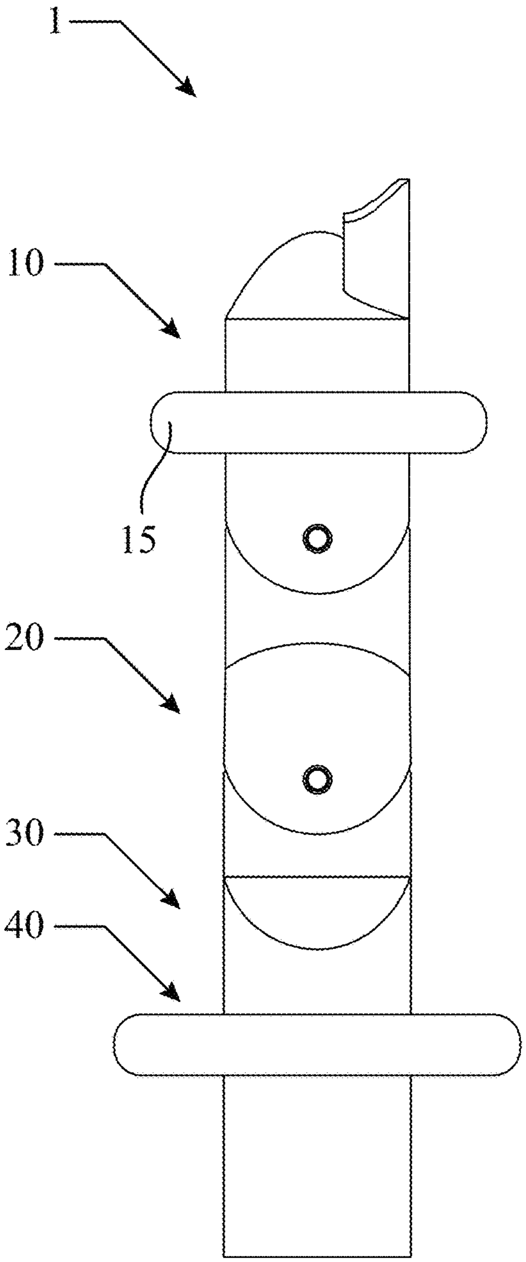
FIG. 10 is a right side view of the assembled upper perspective view of the functional cosmetic prosthetic finger of FIG. 2.

FIG. 10 is a right side view of the assembled upper perspective view of the functional cosmetic prosthetic finger 1 of FIG. 2.

Figure 11:
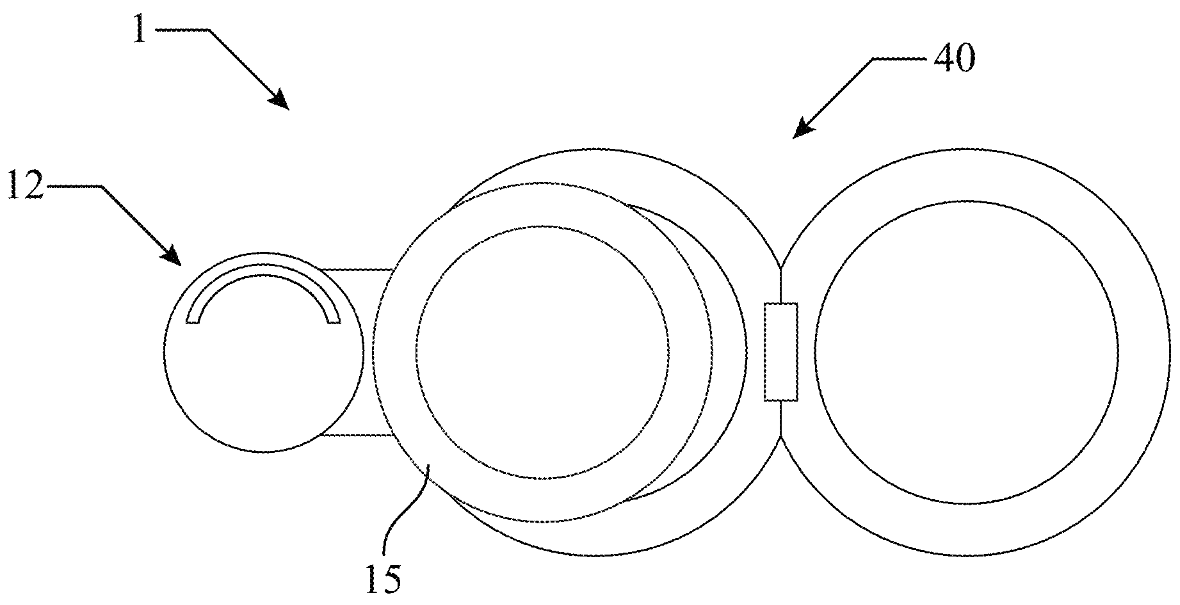
FIG. 11 is a top view of the assembled upper perspective view of the functional cosmetic prosthetic finger of FIG. 2.

FIG. 11 is a top view of the assembled upper perspective view of the functional cosmetic prosthetic finger 1 of FIG. 2.

Figure 12:
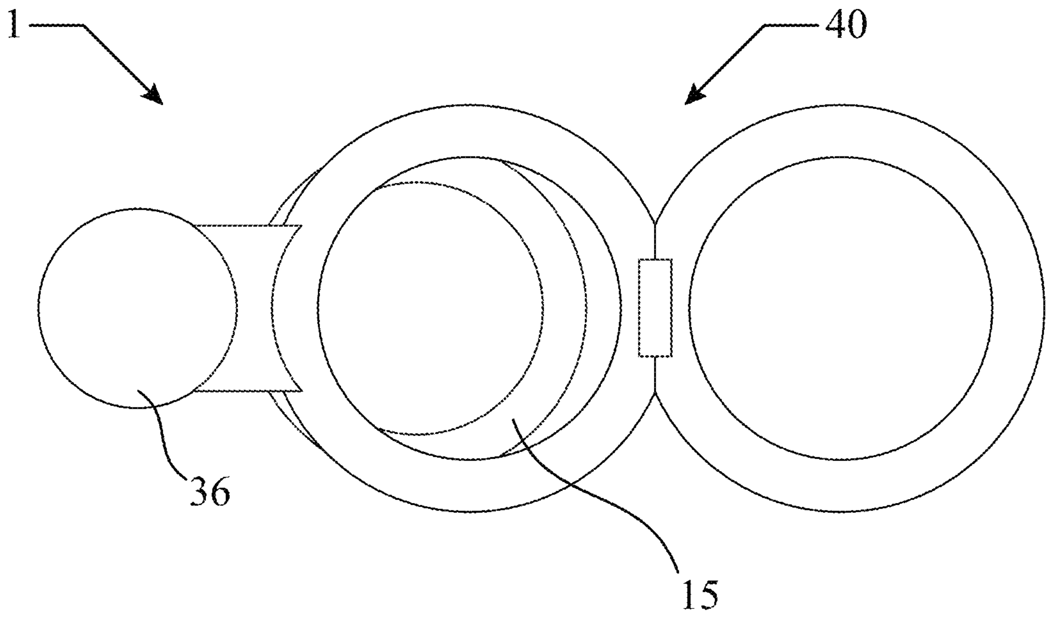
FIG. 12 is a bottom view of the assembled upper perspective view of the functional cosmetic prosthetic finger of FIG. 2.

FIG. 12 is a bottom view of the assembled upper perspective view of the functional cosmetic prosthetic finger 1 of FIG. 2.

Figure 13:
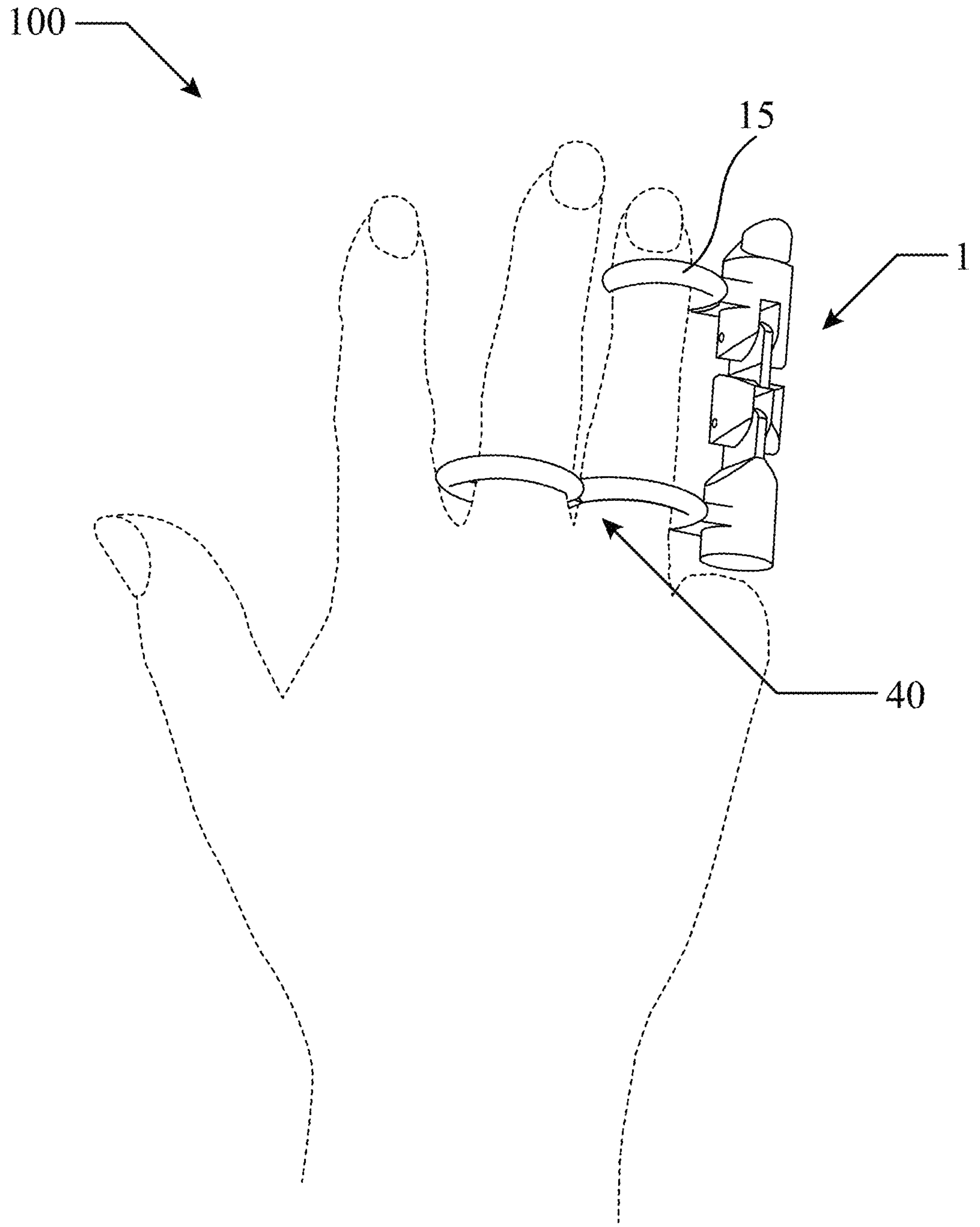
FIG. 13 is a back side perspective view of the functional cosmetic prosthetic finger of the preceding fingers mounted to fingers on a hand to replace a pinky finger.

FIG. 13 is a back side perspective view of the functional cosmetic prosthetic finger 1 of the preceding fingers mounted to fingers on a hand 100 to replace a pinky finger.

Figure 14:
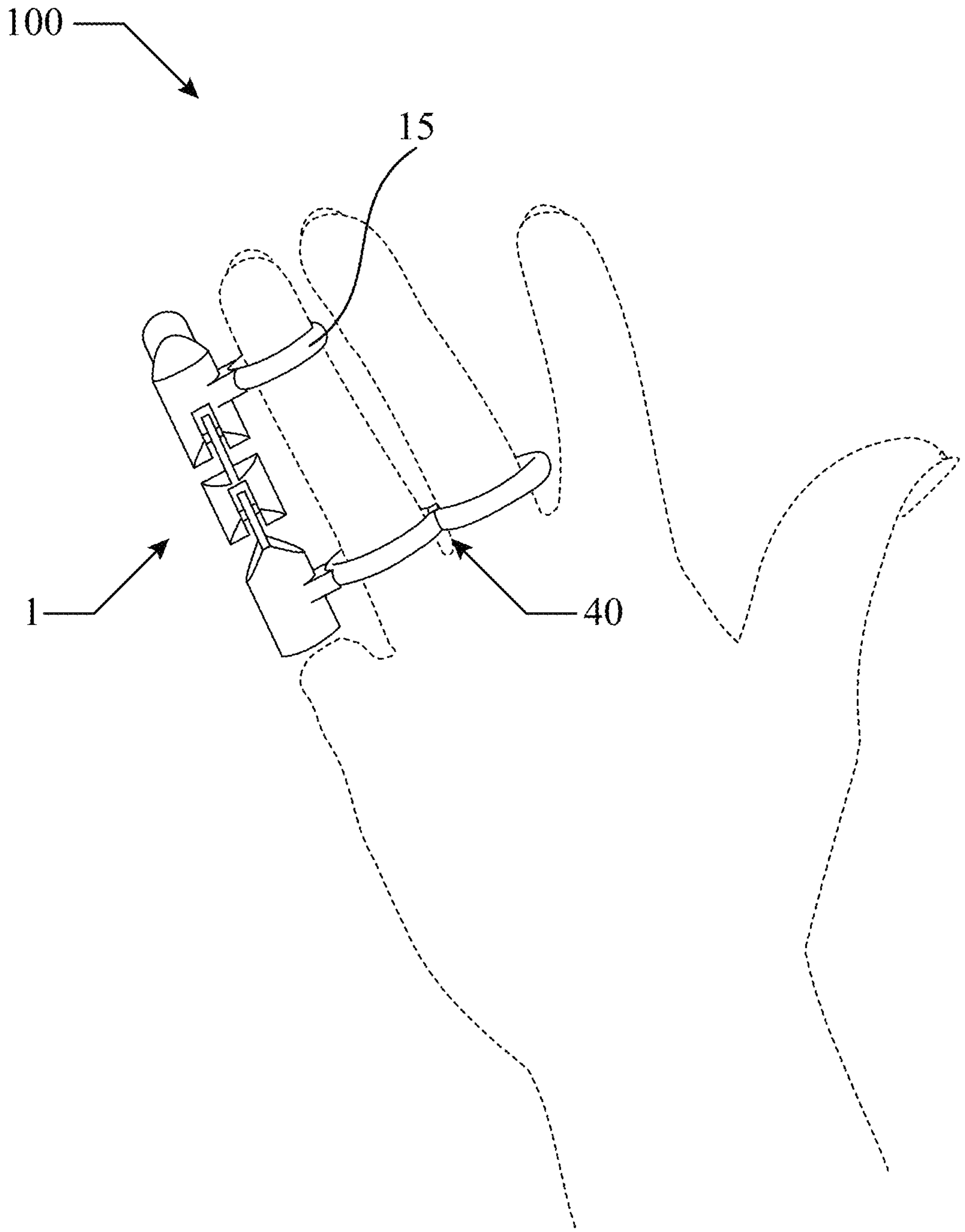
FIG. 14 is a palm side perspective view of the functional cosmetic prosthetic finger of the preceding fingers mounted to fingers on a hand to replace a pinky finger.

FIG. 14 is a palm side perspective view of the functional cosmetic prosthetic finger 1 of the preceding fingers mounted to fingers on a hand 100 to replace a pinky finger.

Figure 15:
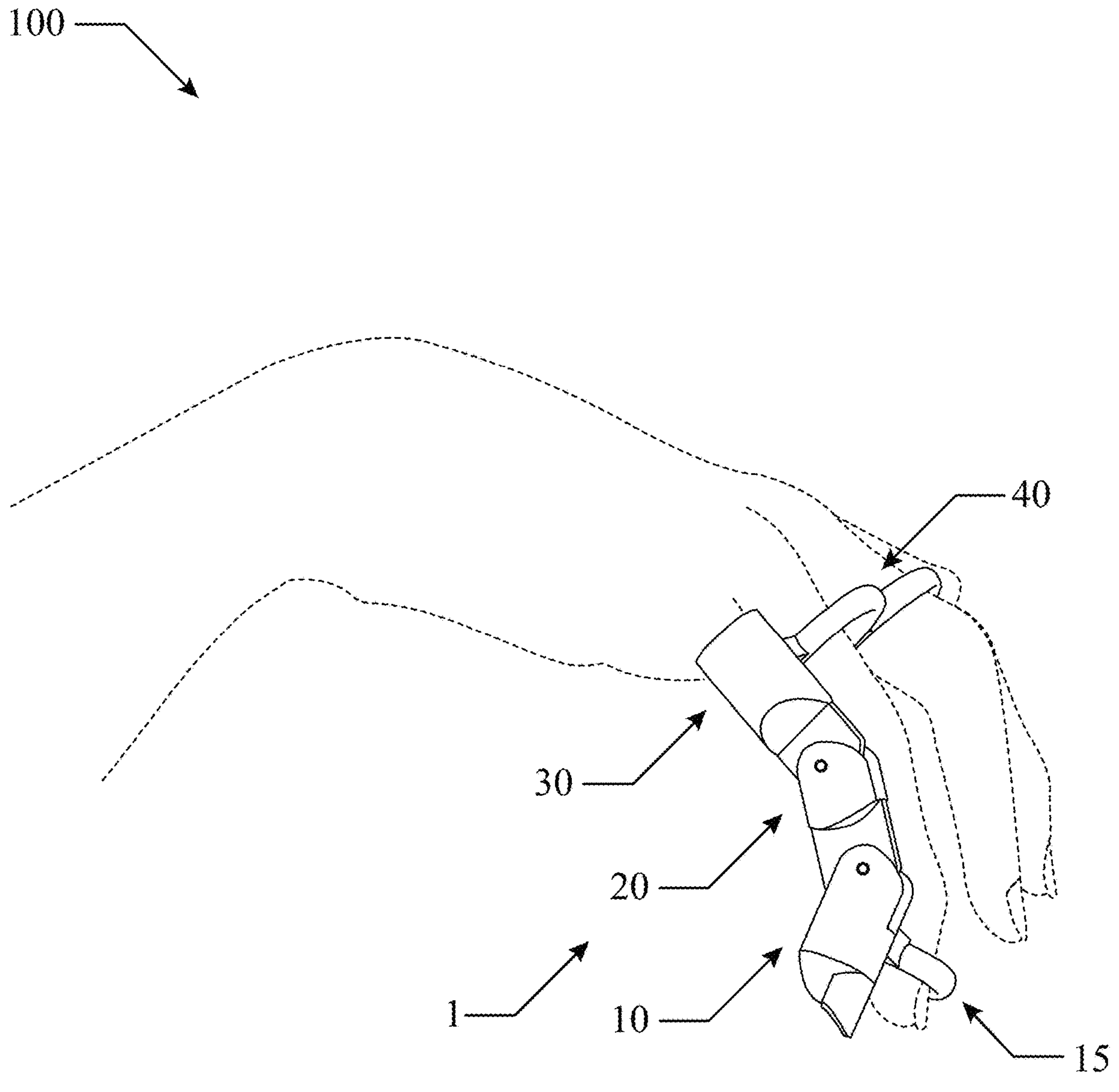
FIG. 15 is a side perspective view of the functional cosmetic prosthetic finger of the preceding fingers mounted to fingers on a hand to replace a pinky finger.

FIG. 15 is a side perspective view of the functional cosmetic prosthetic finger 1 of the preceding fingers mounted to fingers on a hand 100 to replace a pinky finger.

Referring to FIGS. 13-14, the side-by-side rings 40 can be slid over the middle and fourth finger of the hand 100, with the side protruding ring 15 slid over the fourth finger which allows the prosthetic finger 10 for replacing the missing pinky finger.

As the user bends and unbends their middle finger and fourth finger of their hand 10, the functional cosmetic prosthetic finger 1 bends in unison.

With the assembled prosthetic finger 1 in place, the user can move their hand with the prosthetic finger 1. So, as the user extends and straightens their fingers apart and clenches their fingers, the prosthetic finger 1 on the pinky moves with the third finger.

Although the preferred embodiment shows the functional cosmetic prosthetic finger 1 to replace a missing pinky finger, it can be modified as needed to replace other missing fingers. The functional cosmetic prosthetic finger 1 can be modified to replace a missing fourth finger. The functional cosmetic prosthetic finger 1 can be modified to replace a missing middle finger. The functional cosmetic prosthetic finger 1 can be modified to replace a missing index finger as needed While a preferred embodiment of the novel prosthetic finger 1 can be formed from injection molded plastic, the novel prosthetic finger 1 can be made aesthetically pleasing with a fusion of high-tech robotics meets steampunk design, softened with a metallic shine, still lending to realistic mobility and a natural function.

The cosmetic device can be made from plastic, composites, metals, combinations thereof, different colors, and the like. The nail part of the prosthetic finger can be colored to match the nail color on adjacent colored nails.

As discussed, a preferred embodiment is for use of the prosthetic finger being used in place of a missing pinky finger, the invention could be modified and used as a replacement for other fingers/digits of one's hand.

The invention can also be used and modified as needed to be used for a missing toe, such as the big toe, pinky toe and any toe in between.

Because this design is fully customizable by the user, unlike previous art, there is no need for the user to submit documentation in order for the device to be built, such as needing to take measurements or sending photos of the hand. This device is a one size fits all product, which also streamlines the production process, as well as keeping the price point and cost to manufacture at a minimal and reasonable rate, as well as keeping the purchase point of cost extremely low and affordable to the general public.

In describing this invention to the general public, it's as simple as telling a user to slide a few rings on their adjacent fingers to the missing digit, no different than putting on their everyday jewelry. Their adjacent fingers not only stabilize the prosthesis, but also control the jointed movement. If the user finds that the rings need to be adjusted for size, they can either utilize ring sizers to wrap around the stabilization rings, or put their own rings on their fingers first, and then slide the device over the top of the existing rings.

Novel concepts of this product, the Functional Cosmetic Prosthetic Finger, include: (a) Being able to replace a missing digit for cosmetic and functionality reasoning without depending upon a residual stump or partial phalanx to be anchored to (b) Cost effectiveness to be much lower due to the ability of user customization rather than being custom built, thus the difference between previous art, which may possibly be in the thousands of dollars, to the estimated projections of cost for this product to be in the hundreds (c) Utilization of anchoring rings to two digits for stability, disallowing any rotation while wearing the device (d) Ability to self customize the appearance by attaching a cosmetic fingernail (e) Allowance for self customization is a novel idea that allows for the ever changing landscape of the musculature and structure of a hand that has been or will be put through multiple surgeries, allowing for changes in size of fingers due to muscle and ligament swelling and water retention or loss during not only the healing process, but also the changes in musculature due to daily use and overuse of fingers.

Although specific advantages have been enumerated above, various embodiments may include some, none, or all of the enumerated advantages.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A functional cosmetic prosthetic finger for a missing finger, comprising:

a generally cylindrical lower member having an upper end and a lower end;

side-by-side rings extending sideways from a side of the lower member;

a generally cylindrical middle member having an upper end and a lower end, the lower end of the middle member being pivotally attached to the upper end of the lower member;

a generally cylindrical upper member having an upper end a lower end, and having an additional ring extending sideways from a side of the upper member, the lower end of the upper member being pivotally attached to the upper end of the middle member, and wherein the lower end of the lower member is adapted to be positioned adjacent to what would be a knuckle of the missing finger, while one of the side-by-side rings, and the additional ring are adapted to be slid over another finger, and another of the side-by-side rings is adapted to be slid over a still another finger, so that prosthetic finger bends at pivotal connections in unison with the another finger and the still another finger bending in position.

2. The functional cosmetic prosthetic finger of claim 1, wherein the missing finger is a missing pinky finger.

3. The functional cosmetic prosthetic finger of claim 1, wherein the missing finger is a missing fourth finger.

4. The functional cosmetic prosthetic finger of claim 1, wherein the missing finger is a missing middle finger.

5. The functional cosmetic prosthetic finger of claim 1, wherein the missing finger is a missing index finger.

6. The functional cosmetic prosthetic finger of claim 1, wherein the upper member with the one sideways ring, the middle member, and the lower member with the side-by-side rings are formed from plastic.

7. The functional cosmetic prosthetic finger of claim 1, wherein the upper member with the one sideways ring, the middle member, the lower member with the side-by-side rings are formed from metal.

8. The functional cosmetic prosthetic finger of claim 1, wherein the lower end of the middle member being pivotally attached to the upper end of the lower member includes:

the lower end of the middle finger comprises a lower facing channel formed between a pair of downwardly extending side walls; and the upper end of the lower member comprises an upper extending protruding tab; and a lower pin for pivotally attaching the middle member to the lower member.

9. The functional cosmetic prosthetic finger of claim 8, wherein the lower end of the upper member being pivotally attached to the upper end of the middle member includes:

the lower end of the upper finger comprises another lower facing channel formed between a pair of downwardly extending side walls; and the upper end of the middle member comprises another upper extending protruding tab; and an upper pin for pivotally attaching the upper member to the middle member.

10. A functional cosmetic prosthetic finger for a missing finger, comprising:

a generally lower member having an upper end and a lower end;

side-by-side rings extending sideways from a side of the lower member;

a middle member having an upper end and a lower end, the lower end of the middle member being pivotally attached to the upper end of the lower member;

an upper member having an upper end a lower end, and having one ring extending sideways from a side of the upper member, the lower end of the upper member being pivotally attached to the upper end of the middle member, wherein the lower end of the lower member is adapted to be positioned adjacent to what would be a knuckle of the missing finger, while one of the side by side rings, and the one ring are adapted to be slid over another finger, and another one of the side-by-side rings is adapted to be slid over a still another finger, so that prosthetic finger bends at pivotal connections in unison with the another finger and the still another finger bending in position.

11. The functional cosmetic prosthetic finger of claim 10, wherein the lower end of the middle member being pivotally attached to the upper end of the lower member includes:

the lower end of the middle finger comprises a lower facing channel formed between a pair of downwardly extending side walls; and the upper end of the lower member comprises an upper extending protruding tab; and a lower pin for pivotally attaching the middle member to the lower member.

12. The functional cosmetic prosthetic finger of claim 11, wherein the lower end of the upper member being pivotally attached to the upper end of the middle member includes:

the lower end of the upper finger comprises another lower facing channel formed between a pair of downwardly extending side walls; and the upper end of the middle member comprises another upper extending protruding tab; and an upper pin for pivotally attaching the upper member to the middle member.

13. The functional cosmetic prosthetic finger of claim 10, wherein the missing finger is a missing pinky finger.

14. The functional cosmetic prosthetic finger of claim 10, wherein the missing finger is a missing fourth finger.

15. The functional cosmetic prosthetic finger of claim 10, wherein the missing finger is a missing middle finger.

16. The functional cosmetic prosthetic finger of claim 10, wherein the missing finger is a missing index finger.

17. The functional cosmetic prosthetic finger of claim 10, wherein the upper member with the one sideways ring, the middle member, and the lower member with the side-by-side rings are formed from plastic.

18. The functional cosmetic prosthetic finger of claim 10, wherein the upper member with one sideways ring, the middle member, and the lower member with the side-by-side rings are formed from metal.

19. A functional prosthetic finger for a missing finger, comprising:

a lower member having an upper end and a lower end;

side-by-side rings extending sideways from a side of the lower member;

a middle member having an upper end and a lower end, the lower end of the middle member being pivotally attached to the upper end of the lower member;

an upper member having an upper end a lower end, and having another ring extending sideways from a side of the upper member, the lower end of the upper member being pivotally attached to the upper end of the middle member, wherein the lower end of the lower member is adapted to be positioned adjacent to what would be a knuckle of the missing finger, while one of the side by side rings, and the another ring are adapted to be slid over another finger, and another one of the side-by-side rings is adapted to be slid over a still another finger, so that prosthetic finger bends in unison with both the another finger and the still another finger bending in position.

* * * * *